US008814361B2

(12) United States Patent
Granger et al.

(10) Patent No.: US 8,814,361 B2
(45) Date of Patent: Aug. 26, 2014

(54) METHOD FOR DETERMINING THE ACCEPTANCE OF PROGRESSIVE ADDITION LENSES

(75) Inventors: Bérangère Granger, Champigny-sur-Marne (FR); Tara Lynn Alvarez, Whippany, NJ (US)

(73) Assignees: New Jersey Institute of Technology, Newark, NJ (US); Essilor International (Compagnie Generale d'Optique), Charenton le Pont (FR)

( * ) Notice: Subject to any disclaimer, the term of this patent is extended or adjusted under 35 U.S.C. 154(b) by 171 days.

(21) Appl. No.: 13/561,942

(22) Filed: Jul. 30, 2012

(65) Prior Publication Data

US 2014/0028972 A1 Jan. 30, 2014

(51) Int. Cl.
*A61B 3/00* (2006.01)
(52) U.S. Cl.
USPC .......................................................... 351/246
(58) Field of Classification Search
USPC ........................................ 351/246, 203, 201
See application file for complete search history.

(56) References Cited

U.S. PATENT DOCUMENTS

| 5,270,745 A | 12/1993 | Pedrono |
| 7,972,000 B2* | 7/2011 | Becker et al. .................. 351/246 |
| 2012/0105609 A1 | 5/2012 | Qi |

FOREIGN PATENT DOCUMENTS

| EP | 2 395 386 | 12/2011 |
| JP | 2010-099335 | 5/2010 |
| WO | WO 01/62139 | 8/2001 |

OTHER PUBLICATIONS

Kommerell et al. "Heterophoria and Fixation Disparity: A Review", Part I, vol. 8, No. 2, Mar. 21, 2000, pp. 127-134.
Kim et al., "The Relationship Between Phoria and the Ratio of Convergence Peak Velocity to Divergence Peak Velocity", vol. 51, No. 8, Mar. 24, 2010, pp. 4017-4027.

* cited by examiner

*Primary Examiner* — Hung Dang
(74) *Attorney, Agent, or Firm* — Cozen O'Connor

(57) ABSTRACT

Method for determining the acceptance of progressive addition lenses of a wearer, the method comprising: a fusional vergence parameter providing step during which at least one fusional vergence parameter representing the fusional vergence of the wearer is provided, an acceptance determining step during which the value of the at least one fusional vergence parameter is compared to a predetermined threshold value so as to determine the probability of acceptance of progressive addition lens of the wearer.

14 Claims, 2 Drawing Sheets

METHOD FOR DETERMINING THE ACCEPTANCE OF PROGRESSIVE ADDITION LENSES

FIELD OF THE INVENTION

The invention relates to a method for determining the acceptance of progressive addition lenses of a wearer.

BACKGROUND OF THE INVENTION

The discussion of the background of the invention herein is included to explain the context of the invention. This is not to be taken as an admission that any of the material referred to was published, known or part of the common general knowledge at the priority date of any of the claims.

Ophthalmic lenses intended to be held in a frame usually involve a prescription. The ophthalmic prescription can include a positive or negative power prescription as well as an astigmatism prescription. These prescriptions correspond to corrections enabling the wearer of the lenses to correct defects of his vision. A lens is fitted in the frame in accordance with the prescription and with the position of the wearer's eyes relative to the frame.

For presbyopic wearers, the value of the power correction is different for far vision and near vision, due to the difficulties of accommodation in near vision.

The prescription thus comprises a far-vision power value and an addition, or power progression, representing the power increment between far vision and near vision; this comes down to a far-vision power prescription and a near-vision power prescription. Lenses suitable for presbyopic wearers are progressive addition lenses. Examples of progressive addition lenses are described in U.S. Pat. No. 5,270,745.

Progressive addition ophthalmic lenses include a far-vision zone, a near-vision zone and an intermediate-vision zone, a principal progression meridian crossing these three zones. They are generally determined by optimization, based on a certain number of constraints imposed on the different features of the lens.

Some wearers may have difficulties to adapt to the use of progressive addition lenses despite normal binocular vision and other normal clinical findings.

There is a need for simple and reliable tests to try to determine if a wearer is likely to accept or not the use of progressive addition lenses.

Clinical indicators that potentially predict non acceptance of progressive addition lenses may include strabismus, amblyopia, anisometropia, convergence insufficiency or retinal diseases in general.

Linking the above mentioned clinical indicators to the acceptance of progressive addition lenses appears not to be exhaustive and always very reliable.

Therefore, there is a need for a reliable and simple method for determining the acceptance of progressive addition lenses of a wearer.

One object of the invention is to provide a method for determining the acceptance of progressive addition lenses of a wearer that does not present the drawbacks mentioned hereinabove.

SUMMARY OF THE INVENTION

To this end, one aspect of the invention is directed to a method for determining the acceptance of progressive addition lenses of a wearer, the method comprising:

a fusional vergence parameter providing step during which at least one fusional vergence parameter representing the fusional vergence of the wearer is provided, an acceptance determining step during which the value of the at least one fusional vergence parameter is compared to a predetermined threshold value so as to determine the probability of acceptance of progressive addition lens of the wearer.

The inventors have observed that fusional vergence is a reliable and simply measured indicator of the acceptance of progressive addition lenses of a wearer. Indeed, there appears to be a high correlation between the fusional vergence of a wearer and the capacity of the wearer to accept progressive addition lenses.

According to further embodiments which can be considered alone or in combination:

the fusional vergence parameter comprises the rate of phoria adaptation of the wearer; and/or the rate of phoria adaptation is obtained by measuring the dissociated phoria of the wearer having the wearer fix visual targets at a plurality of different distances; and/or the fusional vergence parameter is obtained by a measurement method comprising:

a first distance measurement step during which at least one first phoria measurement is carried out having the wearer fix a visual target at a first distance, a second distance measurement step during which at least two successive phoria measurements are carried out having the wearer fix a visual target at a second distance, the fusional vergence parameter being defined by the equation:

$$FCP = \frac{FPM - IPM}{T},$$

with

FCP being the rate of phoria adaptation,

FPM being the value of the last phoria measurement obtained during the second distance measurement step, IPM being the value of the phoria measurement obtained during the first distance measurement step, T being the time constant of the exponential fit of the phoria measurements obtained during the first and second distance measurement steps; and/or the first and second distances are selected in the list consisting of near vision distance, far vision distance and intermediate vision distance; and/or the first distance is far vision distance and the second distance is near vision distance; and/or the method further comprises, prior to the first distance measurement step, a free fusional stimuli step during which the wearer is placed in an environment substantially free of fusional stimuli; and/or the threshold value is set to three prism diopters per minute and the wearer is considered accepting progressive ophthalmic lens when the fusional vergence parameter is greater than the threshold value; and/or the fusional vergence parameter comprises the vergence facility of the wearer; and/or the fusional vergence parameter is obtained by determining the number of changes in vergence fixation of the wearer when fixing a target at a third distance over a given period of time; and/or the third distance corresponds to a near vision distance or an intermediate vision distance; and/or the threshold value is set to twenty fixations viewing the target as single and clear per minute and the wearer is considered accepting progressive ophthalmic lens when the fusional vergence parameter is greater than the threshold value.

Another aspect of the invention relates to a computer program product comprising one or more stored sequence of instructions that is accessible to a processor and which, when executed by the processor, causes the processor to carry out the steps of the method according to the invention.

Another aspect of the invention relates to a computer-readable medium carrying one or more sequences of instructions of the computer program product of the invention.

Another aspect of the invention relates to a program which makes a computer execute the method according to the invention.

Another aspect of the invention relates to a computer-readable storage medium having a program recorded thereon; where the program makes the computer execute the method according to the invention.

Another aspect of the invention relates to a device comprising a processor adapted to store one or more sequence of instructions and to carry out the steps of the method according to the invention.

Unless specifically stated otherwise, as apparent from the following discussions, it is appreciated that throughout the specification discussions utilizing terms such as "computing", "calculating", "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Non limiting embodiments of the invention will now be described with reference to the accompanying drawing wherein.

DETAILED DESCRIPTION OF THE DRAWINGS

Figure 1:
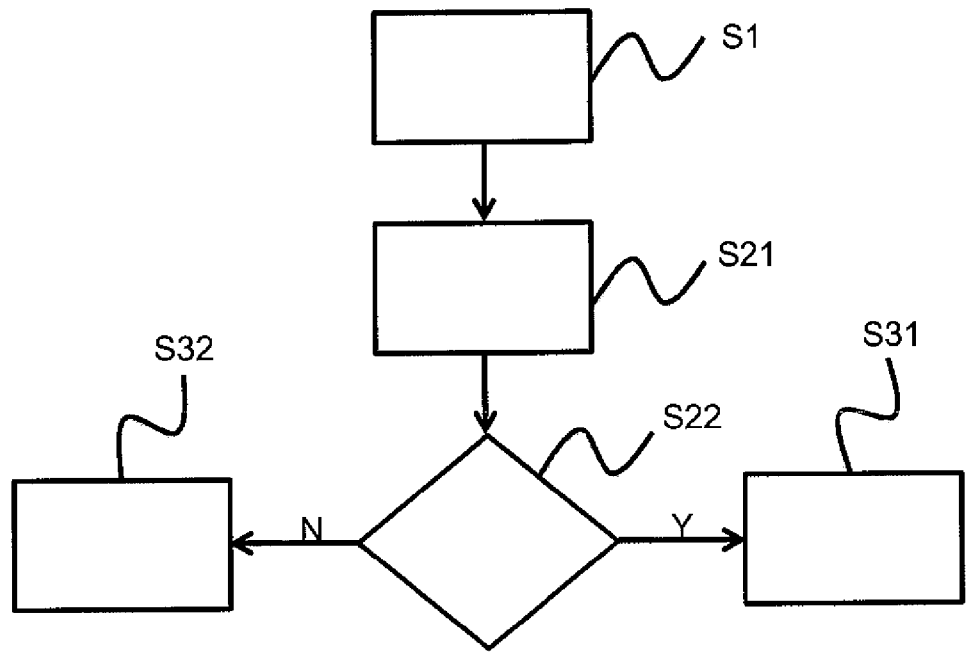
FIG. 1 is a representation of the different steps of a method according to the invention.

According to an embodiment of the invention illustrated on FIG. 1, the method according to the invention comprises a fusional vergence parameter providing step S1, and an acceptance determining step S21 and S22.

During the fusional vergence parameter providing step S1, at least one fusional vergence parameter representing the fusional vergence of the wearer is provided.

The fusional vergence parameter may comprise the rate of phoria adaptation or the vergence facility of the wearer.

According to an embodiment of the invention, during the fusion vergence parameter providing step a plurality of fusional vergence parameter may be provided, in order to improve the overall accuracy of the method.

For example, during the fusion vergence parameter providing step, the rate of phoria adaptation and the vergence facility of the wearer may be provided.

During the acceptance determining step S2, the value of the at least one fusional vergence parameter is compared to a predetermined threshold value so as to determine the probability of acceptance of progressive addition lenses of the wearer.

According to the embodiment represented on FIG. 1, the acceptance determining step S2, may comprise a comparative step S21 and a test step S22.

During the comparative step S21, the value of the fusional vergence parameter is compared to a predetermined threshold value.

The predetermined threshold value depends on the fusional vergence parameter provided during the fusional vergence parameter providing step.

The predetermined threshold value may be adapted according to the proportion or probability of acceptance whished. For example, the threshold value may be predetermined to that substantially all the wearer having a fusional vergence parameter greater than the threshold value accept progressive addition lens. The threshold value may be predetermined to that substantially 50% of the wearer having a fusional vergence parameter greater than the threshold value accept progressive addition lens.

In other words, the predetermined threshold value may be adapted by the operator, lens provider or eye care or retail optician.

During the test step S22, the result of the comparison of the fusional vergence parameter and the predetermined threshold value is tested.

For example, if the fusional vergence parameter is greater than the predetermined threshold value the optician may propose progressive ophthalmic lenses to the wearer in step 31;

whereas if the fusional vergence parameter is smaller than the predetermined threshold value the optician may propose other type of ophthalmic lenses to the wearer.

According to embodiments of the invention having a plurality of fusional vergence parameter each fusional vergence parameter is compared to a predetermined threshold value.

When a plurality of fusional vergence parameters are provided during the fusional vergence parameter providing step the predetermined threshold value for each fusional parameter may be different than each fusional vergence parameters provided individually.

For example, the inventors have observed that the threshold value correspond to substantially 100% of acceptance when only the rate of phoria adaptation is considered is about 3 prism diopters per minute and when only the vergence facility is considered is about twenty fixations per minute; whereas when both fusional vergence parameters are considered, each threshold value may be reduced.

As indicated previously, the fusional vergence parameter may comprise the rate of phoria adaptation of the wearer.

According to an embodiment of the invention, the rate of phoria adaptation is obtained by measuring the phoria of the wearer having the wearer fix visual targets at a plurality of different distances, in order to measure the rate of phoria at different distances. For example, the different distances may correspond to far vision distance, intermediate vision distance and near vision distance.

Figure 2:
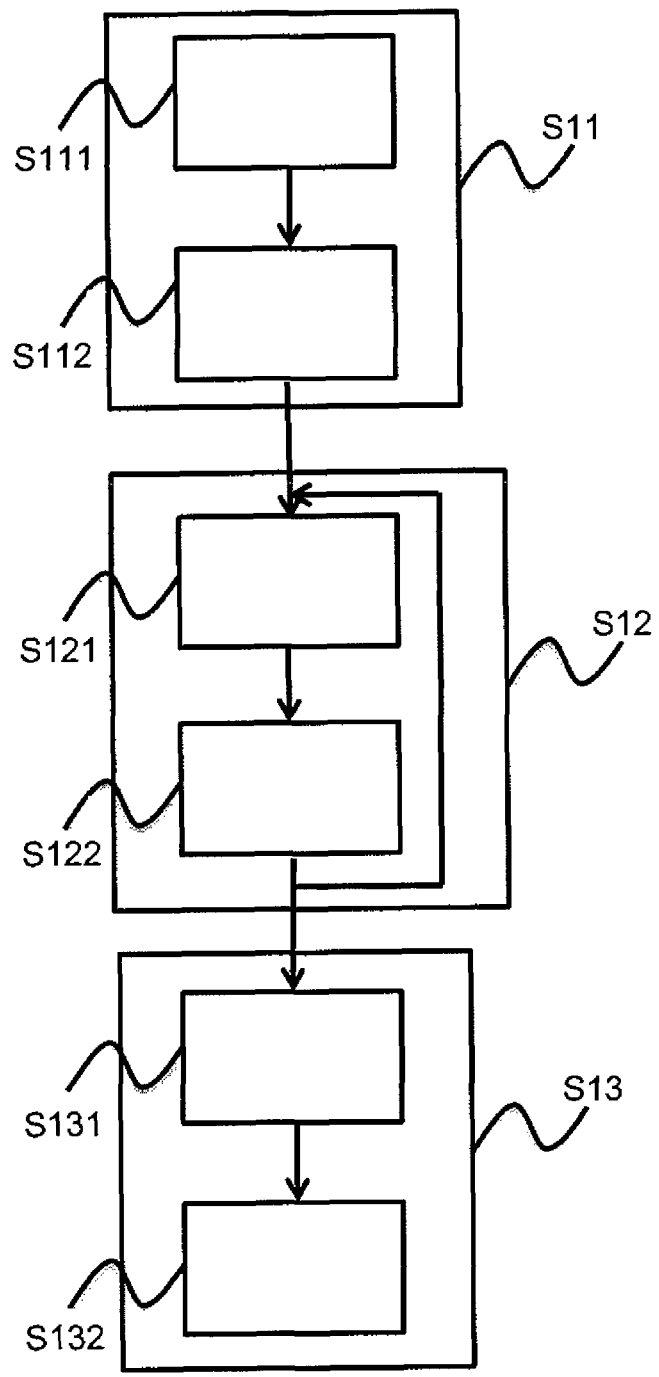
FIG. 2 is a representation of the different steps of a method for measuring rate of phoria adaptation according to the invention.

As illustrated on FIG. 2, the fusional vergence parameter provided during the fusional vergence parameter providing step may be obtained by a rate of phoria adaptation measurement method comprising:
 a first distance measurement step S11,
 a second distance measurement step S12, and
 a fusional vergence parameter determining step S13.

According to the embodiment represented on FIG. 2, the first distance measurement step S11 comprises a first distance fixing step S111 and a first phoria measurement step S112.

During the first distance fixing step S111, the wearer fixes a first visual target placed at a first distance. The first distance may be far vision distance, for example 2 meters.

During the first phoria measurement step S112, the phoria of the wearer is measured while he fixes the first visual target. The phoria may be measured using a cover test or a Maddox rod or any similar clinical approach known from the person skilled in the art.

So as to increase the accuracy of the first phoria measurement, the first distance fixing step S111 has a duration greater than or equal to 1 minute, for example greater than or equal to 2 minutes and 30 seconds.

So as to reduce a possible fatigue effect of the wearer, the first distance fixing step S111 has a duration smaller than or equal to 5 minutes, for example smaller than or equal to 3 minutes and 30 seconds.

According to the embodiment represented on FIG. 2, the second distance measurement step S12 comprises a second distance fixing step S121 and a second phoria measurement step S122.

During the second distance fixing step S121, the wearer fixes a second visual target placed at a second distance. The second distance may be intermediate or near vision distance, for example the second visual target is placed at 40 cm of the wearer.

During the second phoria measurement step S122, the phoria of the wearer is measured while he fixes the second visual target. The phoria may be measured using a Maddox rod or any similar clinical approach known from the person skilled in the art.

The second distance fixing step S121 and a second phoria measurement step S122 are repeated at least twice so as to provide significant results.

According to an embodiment, the phoria of the wearer may be measured periodically during the second distance measurement step S12, the second distance measurement step S12 having a duration greater or equal to 2 minutes, for example greater than or equal to 4 minutes, so as to improve the accuracy of the overall method, and smaller than or equal to 8 minutes, for example smaller than or equal to 6 minutes so as to avoid a possible fatigue effect of the wearer. Furthermore, the inventors have observed that after about 8 minutes, the phoria measurements obtained while having the wearer fixate on a near vision target stabilizes therefore further measurement would not provide further information on the rate of phoria adaptation.

For example, during the second distance measurement step S12, the phoria of the wearer may be measured every 30 seconds while the wearer fixes a near vision target for about 5 minutes.

According to the embodiment represented on FIG. 2, the fusional vergence parameter determining step S13 comprises a fitting step S131 and a fusional vergence parameter calculating step S132.

During the fitting step S131, the data of the phoria measurements obtained during the first and second distance measurement steps versus time are fitted with an exponential fit so as to determine a corresponding time constant.

The fusional vergence parameter may be calculated during the fusional vergence parameter calculating step S132 using the following equation:

$$FCP = \frac{FPM - IPM}{T},$$

with
 FCP being the fusional vergence parameter representing the rate of phoria adaptation,
 FPM being the value of the last phoria measurement obtained during the second distance measurement step,
 IPM being the value of the phoria measurement obtained during the first distance measurement step, and
 T being the time constant of the exponential fit of the phoria measurements obtained during the first and second distance measurement steps, determined for example, during the fitting step S131.

According to an embodiment of the invention, prior to the first distance measurement step S11, the method may comprise a free fusional stimulus step during which the wearer is placed in an environment substantially free of fusional stimulus.

Advantageously, placing the wearer in an environment substantially free of fusional stimulus prior to the first distance measurement step S11, reduces variability. In other words, the variability of the phoria measurements, in particular due to the activity the wearer might have had prior to the method, is reduced.

The free of fusional stimulus environment may be obtained by having the wearer use monocular vision for 3 to 7 minutes, for example for 5 minutes.

According to an embodiment of the invention prior to the first distance measurement step S11, the wearer may be placed in free-visual stimulus environment for a time greater than or equal to 3 minutes and smaller than or equal to 7 minutes, for example about 5 minutes.

The free visual stimulus may be obtained by placing the wearer in a dark room or having the wearer close his eyes.

According to an embodiment of the invention, after the free fusional stimulus step an initial phoria measurement may be carried out before the far distance measurement step S11. This initial phoria measurement may then be compared to the far distance phoria measurement so as to control that the wearer has properly understood the phoria measurement method. Indeed, the phoria of the wearer after having fixated on a far target for a given time should be more exo than the initial phoria measured after the free fusional stimulus step.

The inventors have determined that when measuring the rate of phoria adaptation after having placed the wearer in a substantially free of fusional stimulus environment a correlation appears between the rate of phoria adaptation and the acceptance of progressive addition lenses.

In particular, substantially all of the wearers having a rate of phoria adaptation greater than or equal to three prism diopters per minute accept progressive addition lenses.

Therefore, the predetermined threshold value of the method according to the invention may be set to 3 prism diopters per minute so as to determine if a wearer accepts progressive addition lenses when considering the rate of phoria adaptation of the wearer.

As indicated previously, the fusional vergence parameter may comprise the vergence facility of the wearer.

According to an embodiment of the invention, the vergence facility of the wearer may be determined by quantifying the number of changes in vergence fixation having the wearer fix a third target at a third distance over a given period of time, for example 1 minute. For example the third distance may be near or intermediate vision distance.

Changes in vergence fixation may be generated by prisms, lenses, physical targets, stereoscopes or visual displays. Fixations should be sufficiently long to attain clear single vision of the visual target.

For example, fixation changes may be generated by prisms of 12 base out (BO) and 3 base in (BI) prism diopters.

The inventors have determined that when measuring the vergence facility of the wearer a correlation appears between the number of changes in vergence fixation the wearer can make over a given period of time and the acceptance of progressive addition lenses.

In particular, substantially all of the wearers having at least twenty fixations per minute accept progressive addition lenses.

Therefore, the predetermined threshold value of the method according to the invention may be set to twenty fixations per minute so as to determine if a wearer accepts progressive addition lenses when considering vergence facility of the wearer.

According to a further embodiment of the invention, both vergence facility and rate of phoria adaptation of the wearer can be determined so as to increase the accuracy of the determination of the wearer's acceptance of progressive addition lenses.

Figure 3:
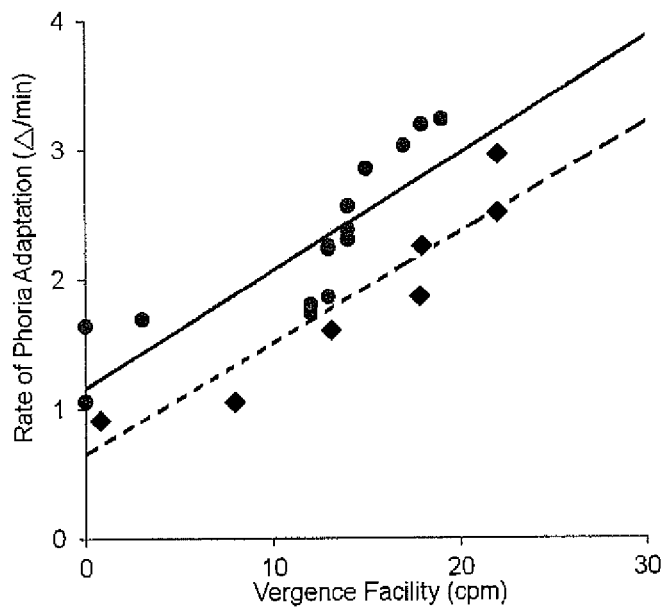
FIG. 3 is a representation of combined data using vergence facility and rate of phoria adaptation to determine a wearer's acceptance of progressive addition lenses.

As illustrated on FIG. 3, the inventors have reported the vergence facility and the rate of phoria adaptation measured on a series of wearer.

Among the wearers who have a rate of phoria adaptation smaller than prism diopters per minute (3 $\Delta$/min) and vergence facility smaller than 22 fixations per minute (cpm), the inventors have reported the wearer that adapted to progressive addition lenses (circles) and those that do not adapt (diamonds).

As it appears on FIG. 3, the data points corresponding to wearers who do not adapt to progressive addition lenses are below the data points corresponding to wearers that adapt.

Hence, the inventors analyzed these data using linear regression of the adapter's data (Y=0.090x+1.16) and compared that to the regression of the non-adapter's data (Y=0.085x+0.65) shown in FIG. 3.

According to an embodiment, a method determining the acceptance of progressive addition lenses of a wearer could comprise:
 a measuring step during which the rate of phoria adaptation and vergence facility are measured;
 a comparing step during which the combined vergence facility and rate of adaptation data point are compared to two different threshold lines, one for adapters (Y=0.090x+1.16) and one for non-adapters (Y=0.085x+0.65).

An analysis that uses a least distance algorithm can determine which threshold line the data point is closer to. Then a probability can be assessed as to whether the wearer has a higher or lower probability of accepting progressive addition lenses.

For example, there may be two threshold lines: one for adapters (unbroken line) and one for non-adapter (broken line).

When a wearer is assessed and his/her rate of adaption is smaller than 3 $\Delta$/min and vergence facility is smaller than 22 cpm then an algorithm may be used to determine whether the combined data point is closer to the unbroken line threshold shown in FIG. 3 suggesting the wearer would accept progressive addition lenses or closer to the broken line suggesting the wearer would not accept progressive addition lenses.

The invention has been described above with the aid of embodiments without limitation of the general inventive concept, as defined in the enclosed set of claims.

The invention claimed is:

1. A method for determining acceptance of progressive addition lenses of a wearer, the method comprising:
 a fusional vergence parameter providing step during which at least one fusional vergence parameter representing the fusional vergence of the wearer is provided; and
 an acceptance determining step during which the value of the at least one fusional vergence parameter is compared to a predetermined threshold value so as to determine the probability of acceptance of progressive addition lens of the wearer.

2. The method according to claim 1, wherein the fusional vergence parameter comprises the rate of phoria adaptation of the wearer.

3. The method according to claim 2, wherein the rate of phoria adaptation is obtained by measuring the dissociated phoria of the wearer having the wearer fix visual targets at a plurality of different distances.

4. The method according to claim 3, wherein the fusional vergence parameter is obtained by a measurement method comprising:
 a first distance measurement step during which at least one first phoria measurement is carried out having the wearer fix a visual target at a first distance; and
 a second distance measurement step during which at least two successive phoria measurements are carried out having the wearer fix a visual target at a second distance, the fusional vergence parameter being defined by the equation:

$$FCP = \frac{FPM - IPM}{T},$$

with
FCP being the rate of phoria adaptation,
FPM being the value of the last phoria measurement obtained during the second distance measurement step,
IPM being the value of the phoria measurement obtained during the first distance measurement step,
T being the time constant of the exponential fit of the phoria measurements obtained during the first and second distance measurement steps.

5. The method according to claim 4, wherein the first and second distances are selected in the list consisting of near vision distance, far vision distance and intermediate vision distance.

6. The method according to claim 4, wherein the first distance is far vision distance and the second distance is near vision distance.

7. The method according to claim 6, further comprising prior to the first distance measurement step a free fusional stimulus step during which the wearer is placed in an environment substantially free of fusional stimulus.

8. The method according to claim 7, wherein the threshold value is set to three prism diopters per minute and the wearer is considered accepting progressive ophthalmic lens when the fusional vergence parameter is greater than the threshold value.

9. The method according to claim 1, wherein the fusional vergence parameter comprises the vergence facility of the wearer.

10. The method according to claim 9, wherein the fusional vergence parameter is obtained by determining the number of changes in vergence fixation of the wearer when fixing a target at a third distance over a given period of time.

11. The method according to claim 10, wherein the third distance corresponds to a near vision distance or an intermediate vision distance.

12. The method according to claim 11, wherein the threshold value is set to twenty fixations per minute and the wearer is considered accepting progressive ophthalmic lens when the fusional vergence parameter is greater than the threshold value.

13. A computer program product comprising one or more stored sequence of instructions that is accessible to a processor and which, when executed by the processor, causes the processor to carry out the steps of claim 1.

14. A computer-readable medium carrying one or more sequences of instructions of the computer program product of claim 13.

* * * * *